(12) United States Patent
Liu et al.

(10) Patent No.: US 10,839,542 B2
(45) Date of Patent: Nov. 17, 2020

(54) SYSTEMS AND METHODS FOR 3D LAPAROSCOPIC SURFACE RECONSTRUCTION

(71) Applicant: The Chinese University of Hong Kong, Hong Kong (CN)

(72) Inventors: Yunhui Liu, Hong Kong (CN); Congying Sui, Hong Kong (CN); Zerui Wang, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 16/260,546

(22) Filed: Jan. 29, 2019

(65) Prior Publication Data
US 2020/0242791 A1 Jul. 30, 2020

(51) Int. Cl.
*G06T 7/593* (2017.01)
*G06K 9/62* (2006.01)
*G06T 7/521* (2017.01)
*H04N 13/254* (2018.01)
*H04N 13/239* (2018.01)
(Continued)

(52) U.S. Cl.
CPC .......... *G06T 7/593* (2017.01); *A61B 1/00177* (2013.01); *A61B 1/00193* (2013.01); *A61B 1/04* (2013.01); *A61B 1/3132* (2013.01); *G06K 9/6202* (2013.01); *G06T 7/521* (2017.01); *H04N 13/239* (2018.05); *H04N 13/254* (2018.05); *G06T 2207/10012* (2013.01); *G06T 2207/10028* (2013.01); *G06T 2207/10068* (2013.01); *H04N 2013/0074* (2013.01)

(58) Field of Classification Search
CPC ............. G06T 7/593; G06T 7/521; G06T 2207/10012; G06T 2207/10028; G06K 9/6202; H04N 13/254; H04N 13/239; H04N 2005/2255; H04N 2013/0081; H04N 13/271; A61B 1/3132; A61B 1/00177; A61B 1/0193; A61B 1/04; A61B 1/00193; A61B 1/00; A61B 1/00009
See application file for complete search history.

(56) References Cited

U.S. PATENT DOCUMENTS

2010/0008588 A1 * 1/2010 Feldkhun ............ G01S 17/48
382/206
2017/0100024 A1 * 4/2017 Shahmoon ........... A61B 1/0017

FOREIGN PATENT DOCUMENTS

CN 102445165 A * 5/2012

OTHER PUBLICATIONS

Mirota et al.; "Vision-Based Navigation in Image-Guided Interventions"; Annu. Rev. Biomed. Eng. 2011; 13:297-319.
(Continued)

*Primary Examiner* — David E Harvey
(74) *Attorney, Agent, or Firm* — Fish & Richardson P.C.

(57) ABSTRACT

Various aspects of a systems and method for reconstructing a surface of a three-dimensional (3D) target are disclosed herein. The method may comprise projecting a sequence of patterns to the surface of the target; capturing a first stereo endoscopic image and a second stereo endoscopic image from the patterns reflected from the surface; performing a coarse matching for the captured first and second stereo endoscopic images to acquire a set of matching candidates; and performing a precise matching for the acquired set of matching candidates to acquire reconstruction pixels for reconstructing the surface.

18 Claims, 9 Drawing Sheets

(51) Int. Cl.
A61B 1/00 (2006.01)
A61B 1/04 (2006.01)
A61B 1/313 (2006.01)
H04N 13/00 (2018.01)

(56) References Cited

OTHER PUBLICATIONS

Malti et al.; "Template-Based Conformal Shape-from-Motion from Registered Laparoscopic Images"; "https://www.researchgate.net/publication/266488629," 2011; 6 pages.
Collins et al.; "Towards Live Monocular 3D Laparoscopy Using Shading and Specularity Information"; IPCAI 2012; LNAI 7330, pp. 11-21.
Stoyanov; "Stereoscopic Scene Flow for Robotic Assisted Minimally Invasive Surgery"; MICCAI 2012, Part I, LNCS 7510, pp. 479-486.
Xu; "A Foldable Stereo Vision Unit for single Port Access Laparoscopy"; 2014 IEEE International Conference on Robotics & Automation (ICRA), Hong Kong Convention and Exhibition Center, May 31-Jun. 7, 2014, Hong Kong China; pp. 4182-4187.
Song et al.; "Dynamic Reconstruction of Deformable Soft-Tissue With Stereo Scope in Minimal Invasive Surgery"; IEEE Robotics and Automation Letters, vol. 3, No. 1, Jan. 2018.
Noonan, et al.; "A Stereoscopic Fibroscope for Camera Motion and 3D Depth Recovery during Minimally Invasive Surgery"; 2009 IEEE International Conference on Robotics and Automation, Kobe International Conference Center, Kobe, Japan; May 12-17, 2009; pp. 4463-4468.
Geng et al.; "Review of 3-D Endoscopic Surface Imaging Techniques"; IEEE Sensors Journal, vol. 14, No. 4, Apr. 2014; pp. 945-960.
Semmler et al.; 3D Reconstruction of Human Laryngeal Dynamics Based on Endoscopic high-Speed Recordings; IEEE Transactions on Medical Imaging, vol. 35, No. 7, Jul. 2016; pp. 1615-1624.
Reiter et al.; "Surgical Structured Light for 3D Minimally Invasive Surgical Imaging"; 2014 IEEE/RSJ International Conference on Intelligent Robots and Systems (IROS 2014); Sep. 14-18, 2014, Chicago, IL; pp. 1282-1287.
Schmalz et al.; "An Endoscopic 3D Scanner Based on Structured Light"; Medical Image Analysis 16 (2012) 1063-1072.
Maier-Hein et al.; "Optical Techniques for 3D Surface Reconstruction in Computer-Assisted Laparoscopic Surgery" Medical Image Analysis 17 (2013) 974-996.
Hayashibe et al.; "Laser-Scan Endoscope System for Intraoperative Geometry Acquisition and Surgical Robot Safety Management"; Medical Image Analysis 10 (2006) 509-519.
Dupont et al.; "Tri-Dimensional Optical Inspection Based on Flexible Image Guide: First Step Toward 3D Industrial Endoscopy"; ASME 2012, 11$^{th}$ Biennial Conference on Engineering Systems Design and Analysis ESDA2012; Jul. 2-4, 2012, Nantes, France.
Hou et al.; "A Compact Active Stereovision System with Dynamic Reconfiguration for Endoscopy or Colonoscopy Applications"; MICCAI 2014, Part I, LNCS 8673, pp. 448-445, 2014.
Van der Jeught et al.; "Real-Time Structured Light Profilometry: A Review"; Optics and Lasers in Engineering 87 (2016) 18-31.
Salvi et al.; "Pattern Codification Strategies in Structured Light Systems"; Pattern Recognition 37 (2004) 827-849.
Moore; "Gradient-Index Optics: A Review"; Applied Optics, vol. 19, No. 7, Apr. 1, 1980; pp. 1035-1038.
Salvi et al.; "A State of the Art in Structured Light Patterns for Surface Profilometry"; Pattern Recognition 43 (2010) 2666-2680.
Wiegmann et al.; "Human Race Measurement by Projecting Bandlimited Random Patterns"; Optic Express, vol. 14, No. 17, Aug. 21, 2006; pp. 7692-7698.

\* cited by examiner

Camera 1          Camera 2

Coarse matching

Precise matching

SYSTEMS AND METHODS FOR 3D LAPAROSCOPIC SURFACE RECONSTRUCTION

TECHNICAL FIELD

The present disclosure generally relates to the field of surface reconstruction, more particularly, to systems and methods for 3D laparoscopic surface reconstruction.

BACKGROUND

Many research groups have been devoted to the endoscopic 3D reconstruction. These techniques are divided into two categories: passive methods and active methods. In passive methods, only images captured from the environment are required for the 3D reconstruction, which is less robust to textureless surface.

Recently, active methods have been proposed in which additional structured light patterns are projected onto the target in order to establish consistent and reliable surface features for 3D reconstruction. Among all the active techniques, multiple-shot structured-light method has been widely developed for its good performance in measurement precision and accuracy. However, a major problem is the time-consuming acquisition of multiple images, which makes the multiple-shot methods unsuitable in dynamic surface measurement. Besides, due to the limitation of the probe size, most of the current 3D laparoscopic surface reconstruction systems utilizing structured light method adopt single-camera single-projector configuration, where correlation is required to be established between the projected patterns and captured images. As a result, illumination changes and disturbances result in wrong matching. Besides, luminance compensation of the cameras and calibration of projector are necessary for current structured-light-based 3D endoscopic systems, which lead to the complex operations.

SUMMARY

According to the present disclosure, a novel 3D laparoscopic surface reconstruction system is designed for application of the active stereo technique in which two image-feedback channels and one pattern-projection channel are integrated, while most state of the art designs utilize only single image channel and single projection channel. The stereo camera configuration enhances the robustness to noises and illumination changes, and simplifies the operations because projector calibration and nonlinear compensation of luminance are not required.

By utilizing the high-resolution fiber bundles and designing customized GRIN lenses, the laparoscopic probe has a suitable field-of-view (FOV) and working distance for automatic robotic surgery, and its diameter is smaller compared with conventional 3D laparoscopes (e.g., 10 mm for Storz 3D laparoscopes).

In the method of the present disclosure, phase maps of different frequencies are utilized in a multi-step matching procedure. With the method, less patterns are required in each reconstruction cycle, compared with those used in the current multiple-shot structured light methods wherein 10-40 patterns are required. Therefore, the proposed method reduces the image acquisition time and makes it suitable for dynamic measurement. Besides, matching efficiency and accuracy are enhanced by the multi-step matching.

In one aspect, the present disclosure provides a method for reconstructing a surface of a three-dimensional (3D) target. The method may comprise projecting a sequence of patterns to the surface of the target; capturing a first stereo endoscopic image and a second stereo endoscopic image from the patterns reflected from the surface; performing a coarse matching for the captured first and second stereo endoscopic images to acquire a set of matching candidates; and performing a precise matching for the acquired set of matching candidates to acquire reconstruction pixels for reconstructing the surface.

In another aspect, the present disclosure provides a system for reconstructing a surface of a three-dimensional (3D) target. The system may comprise a pattern projecting device for projecting a sequence of patterns to the surface of the target; an image capturing device for capturing a first stereo endoscopic image and a second stereo endoscopic image from the patterns reflected from the surface; and a reconstructing device for performing a coarse matching for the captured first and second stereo endoscopic images to acquire a set of matching candidates, and performing a precise matching for the acquired set of matching candidates to acquire reconstruction pixels for reconstructing the surface.

In an aspect, the present disclosure provides a non-transitory computer-readable medium or media comprising one or more sequences of instructions which, when executed by one or more processors, causes steps to be performed, wherein the steps may comprise generating the patterns to be projected including a coarse pattern and a precise pattern; extracting respective codeword maps from the captured first and second stereo endoscopic images by using phases of points in the images, wherein each point in an image has a unique codeword in the codeword map; and performing a coarse matching for the captured first and second stereo endoscopic images to acquire a set of matching candidates, and performing a precise matching for the acquired set of matching candidates to acquire reconstruction pixels for reconstructing the surface.

In another aspect, the present disclosure provides a system for reconstructing a surface of a three-dimensional (3D) target. The system may comprise a pattern projecting device for projecting a sequence of patterns to the surface of the target; an image capturing device for capturing a first stereo endoscopic image and a second stereo endoscopic image from the patterns reflected from the surface; at least one processor; and a memory storing instructions, the instructions when executed by the at least one processor, cause the at least one processor to perform operations, the operations comprising:

generating the patterns to be projected including a coarse pattern and a precise pattern;

extracting respective codeword maps from the captured first and second stereo endoscopic images by using phases of points in the images, wherein each point in an image has a unique codeword in the codeword map; and performing a coarse matching for the captured first and second stereo endoscopic images to acquire a set of matching candidates, and performing a precise matching for the acquired set of matching candidates to acquire reconstruction pixels for reconstructing the surface.

BRIEF DESCRIPTION OF THE DRAWING

Exemplary non-limiting embodiments of the present disclosure are described below with reference to the attached drawings. The drawings are illustrative and generally not to an exact scale. Like reference numerals refer to like parts throughout the various views unless otherwise specified.

DETAILED DESCRIPTION

In order to make the objects, the technical solutions and the advantages of the present disclosure clear and complete, the present disclosure will be described hereinafter in a clear and complete manner in conjunction with the drawings and embodiments. Evidently, the following embodiments merely relate to a part of, rather than all of, the embodiments of the present disclosure, and based on these embodiments, a person skilled in the art may, without any creative effort, obtain other embodiments, which also fall within the scope of the present disclosure.

Figure 1:
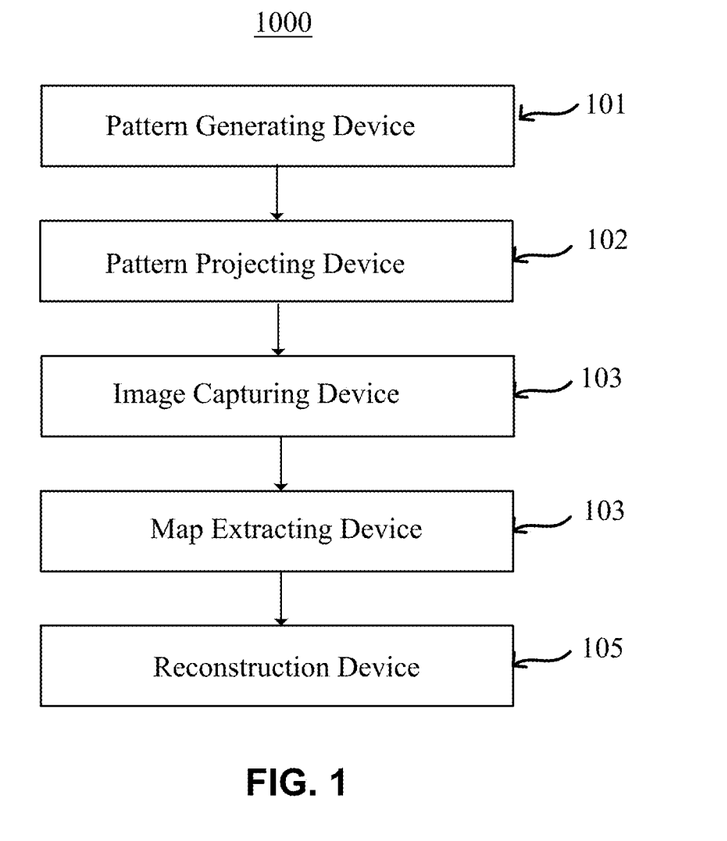
FIG. 1 is a schematic block view illustrating a system for 3D surface reconstruction according to an embodiment of the present disclosure.

FIG. 1 is a schematic view illustrating a system for reconstructing a surface of a 3D target according to an embodiment of the present disclosure. The 3D target may include, but not limited to, laparoscopic tissues, endoscopic tissues, stomach tissues, or anatomical tissues.

As shown in FIG. 1, the system 1000 for reconstructing a surface of a 3D target may include a pattern projecting device 102, an image capturing device 103 and a reconstructing device 105.

The pattern projecting device 102 may project a sequence of patterns to the surface of the target. The projected pattern may be multi-frequency phase shifting fringes. In an embodiment, the patterns may be dual-frequency sinusoidal phase-shifting fringes. The pattern projecting device may include an optic prism for amplifying and projecting patterns.

The image capturing device 103 may capture a first image and a second image from the patterns reflected from the surface. In an embodiment, the captured images are stereo endoscopic images. In an embodiment, the image capturing device may include a left camera and a right camera for capturing the first and second stereo endoscopic image, respectively. The left and right cameras may each include an optic prism for collecting and imaging reflective light. In another embodiment, the image transmission path in the pattern projecting device 102 and the image capturing device 103 are imaging fiber bundles. In another embodiment, the direction of the optic prisms of the left and right cameras of the image capturing device 103 and the optic prisms of the pattern projecting device 102 is changeable.

The reconstructing device 105 may perform a coarse matching and a precise matching for the captured first and second stereo endoscopic images to acquire reconstruction pixels for reconstructing the surface. In an embodiment, the reconstructing device may perform the coarse matching for the captured first and second stereo endoscopic images to acquire a set of matching candidates and perform the precise matching for the acquired set of matching candidates to acquire reconstruction pixels for reconstructing the surface.

In an embodiment, the system 1000 may further include a pattern generating device 101 for generating a coarse pattern. The image capturing device 103 may capture a first coarse image and a second coarse image from the coarse pattern reflected from the surface. For performing the coarse matching, the reconstructing device 105 may generate a first coarse codeword map from the first coarse image and generate a second coarse codeword map from the second coarse image, and determine a group of points in the second coarse image corresponding to each point in the first coarse image, according to the extracted first and second coarse codeword maps so that the candidate pixels in the set of matching candidate may be acquired.

In another embodiment, the pattern generating device 101 may further generate a precise pattern which is different from the coarse pattern. In an embodiment, the coarse pattern may be a phase shifting fringe with a frequency lower than that of the precise pattern.

In an embodiment, the pattern may be dual-frequency sinusoidal phase-shifting fringes including high-frequency sinusoidal phase-shifting fringes and low-frequency sinusoidal phase-shifting fringes. In another embodiment, the total numbers of the dual-frequency sinusoidal phase-shifting fringes are five, wherein the number of high-frequency sinusoidal phase-shifting fringes is 3, and the number of low-frequency sinusoidal phase-shifting fringes is 2.

The image capturing device 103 may further capture a first precise image and a second precise image from the precise pattern reflected from the surface. Then, for performing the precise matching, the reconstructing device 106 may generate a first precise codeword map from the first precise image and a second precise codeword map from the second precise image, and determine, among the candidate pixels in the set of matching candidate, the reconstruction pixels for surface reconstruction according to the extracted first and second codeword maps.

In an embodiment, the system 1000 may further include a map extracting device 104 for extracting respective codeword maps from the captured first and second stereo endoscopic images by using phases of points in the stereo endoscopic images, wherein each point in an image has a unique codeword in the codeword map. In an embodiment, reconstructing device 105 may perform the coarse matching based on the extracted codeword maps to acquire the candidate pixels in a set of matching candidates. In an embodiment, reconstructing device 105 may perform the precise matching for the acquired candidate pixels.

In an embodiment, the pattern projecting device 102 may be a digital light processing (DLP) projector and the image capturing device 103 may be a high-speed camera. In an embodiment, the codeword maps are wrapped phase maps derived from the captured stereo images.

Figure 2:
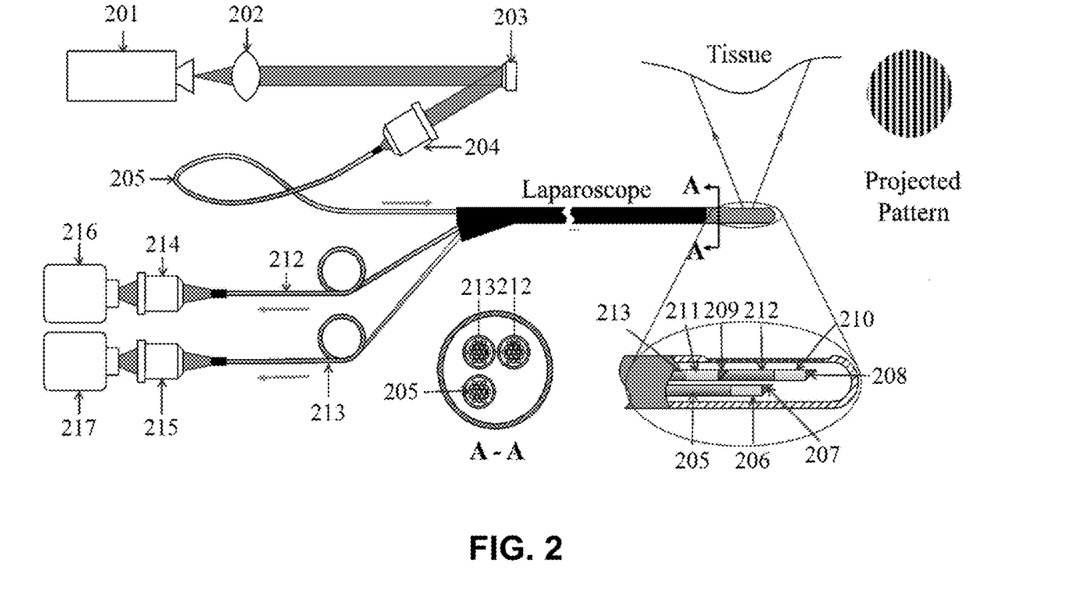
FIG. 2 is a schematic view illustrating an exemplary system of 3D laparoscopic surface reconstruction according to the present disclosure.

FIG. 2 illustrates an exemplary system of the system of 3D laparoscopic surface reconstruction according to the present disclosure.

Although the system of 3D laparoscopic surface reconstruction is shown for illustrative purposes, the techniques described herein are not limited as such. Hereinafter, the configuration of the system will be described in details by describing the light path of the system.

As shown in FIG. 2, the patterns with high speed are generated by the pattern generating device. In this embodiment, the pattern generating device may be configured to generate the required patterns with high speed. The pattern generating device may comprise a light emitting diodes (LED) 201, a collimation optic lens 202, a digital micromirror device (DMD) 203, and an objective lens 204. The DMD 203 consists of 1 million micro mirrors, which can be controlled individually to switch between two states: "ON" and "OFF" with high frequency. The light beam reflected by all the mirrors on the "ON" state forms a pattern, which will be coupled into a fiber bundle through the objective lens. Therefore, desired dynamic patterns can be generated by controlling all the mirrors at the same time.

Figure 3A:
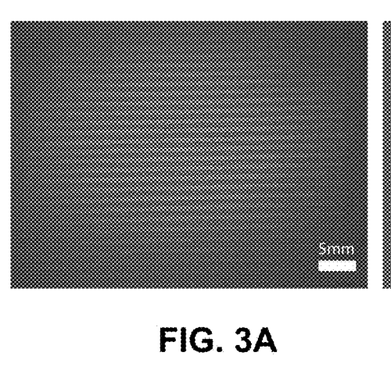
FIG. 3A illustrates an example of fringes generated by DMD.
Figure 3B:
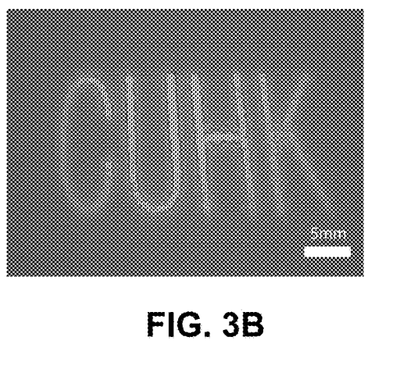
FIG. 3B illustrates an example of pattern "CUHK" generated by DMD according to an embodiment of the present disclosure.

With reference to FIG. 2, two examples of generated patterns are displayed. FIG. 3A illustrates an example of fringes generated by DMD, and FIG. 3B illustrates an example of pattern "CUHK" generated by DMD according to an embodiment of the present disclosure.

Returning to FIG. 2, a beam of light is emitted by the light emitting diodes (LED) 201 and then collimated by the collimation optic lens 202. The digital micromirror device (DMD) 203 reflects the LED beam and produces dynamic patterns, which are coupled into an input fiber bundle 205 through the objective lens 204. The Fiber bundle can transmit high-quality images with small volume.

Figure 4:
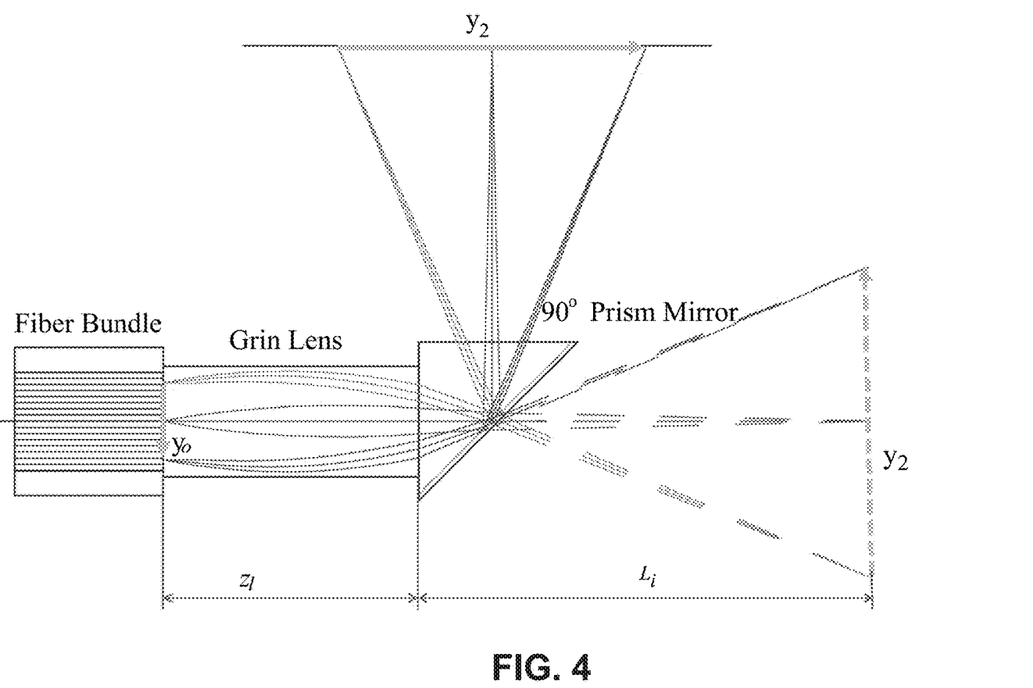
FIG. 4 illustrates an exemplary graph of showing the working principle of GRIN Lens and 90° prim mirror according to another embodiment of the present disclosure.

Then, the generated patterns are transmitted to the other end of the fiber bundle 205, i.e. the laparoscopic probe. In order to amplify and project the designed pattern on the target and focus the reflected light into the fiber bundles, a radial GRIN lens 206 is used, whose index of refraction varies continuously outward from the optical axis, so that the light propagate from the fiber bundle will be gradually focused on the image plane by the GRIN lens, as shown in FIG. 4. FIG. 4 illustrates an exemplary graph of showing the working principle of GRIN Lens and 90° prim mirror according to another embodiment of the present disclosure.

The advantages of GRIN lens over the other tube lenses are that the diameter of GRIN lens is less than 2 mm, which is comparable with the diameter of the image fiber bundle, and its magnification can be large.

In an embodiment, in order to achieve the desired field-of-view (FOV) and working distance, the parameters of the GRIN lens need to be well designed. The relationship among the image distance $L_i$, the magnification M and the length $Z_l$ of the GRIN lens is given by (1) and (2).

$$M = \frac{y_1}{y_0} = \sqrt{\frac{1}{(n_0 L_i g)^2 + 1}} \quad (1)$$

$$Z_l = \frac{\arctan(-n_0 L_i g) + \pi}{g} \quad (2)$$

where $n_0$ is the refractive index at the center, and g is the gradient constant. In addition, $y_0$ and $y_1$ are characteristic lengths of the object and image, respectively. In an exemplary prototype, the diameter of FOV and the working distance of the laparoscopic probe may be designed to be 30-85 mm and 40-100 mm, respectively, which satisfy the requirement of the robotic surgery.

The direction of Grin lenses is restricted to be parallel with the axial direction of the laparoscope. However, due to the limitation of the overall diameter of the laparoscopic probe, the baseline between the two image acquisition GRIN lenses is very short, which leads to low depth resolution. To solve this problem, prism mirrors 207, 209 and 210 as shown in FIG. 2 are employed to reflect the light propagation direction to the lateral side so that sufficient space is available for longer baseline.

Returning to FIG. 2, the GRIN lens 206 and the prism mirror 207 amplify and project the patterns onto the tissue surface of the target, for example, the laparoscopic tissues. Similarly, the patterns reflected by the tissue surface are transmitted back to the output fiber bundles 212 and 213.

Figure 5A:
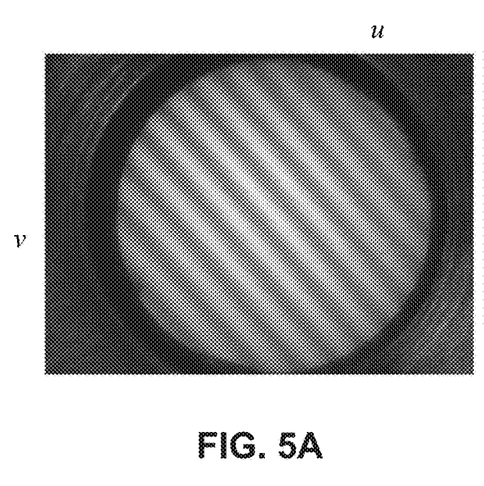
FIGS. 5A and 5B illustrates an exemplary feedback images from two image capturing devices, respectively according to another embodiment of the present disclosure.
Figure 5B:
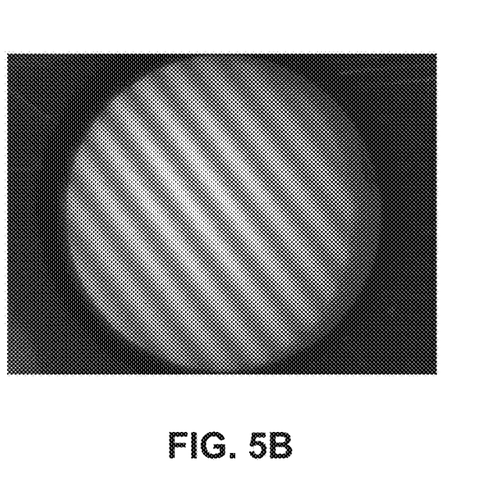

After focused on the end of the fiber bundles 212 and 213 by the GRIN lenses 210 and 211, the feedback image pairs are then transmitted into the image capturing device, where the microscope objective lenses 214 and 215 image the feedback patterns onto the cameras 216 and 217. The customized GRIN lens has a compatible size with the fiber bundle. Its working distance is suitable for automatic robotic surgery. The focusing process is performed by adjusting the axial positions of the objective lenses and cameras, so that the real images focused on the camera sensors occupy the maximum space of the camera chips, as shown in FIGS. 5A and 5B. FIGS. 5A and 5B illustrate an exemplary feedback images from two image capturing devices, respectively according to an embodiment of the present disclosure.

As above, the system of the present disclosure comprises three optic channels, one channel is used for pattern projection and the other two channels are used for image feedback. In the system, high-quality images can be transmitted by the fiber bundle with small volume and the customized GRIN lens has a compatible size with the fiber bundle with working distance suitable for automatic robotic surgery. High-speed cameras and a high-speed pattern projector are deployed. With the system of the present disclosure, the stereo camera configuration enhances the robustness to noises and illumination changes, and simplifies the operations because the projector calibration and nonlinear compensation of luminance are not required.

It should be noted that, although the pattern generating device 101, the map extracting device 104 and the reconstructing device 105 are illustrated separately in FIG. 1, in embodiments, a single computing device may operate as one or more of the pattern generating device 101, the map extracting device 104 and the reconstructing device 105.

Hereinafter a method for reconstructing the surface of the 3D target will be described.

Figure 6:
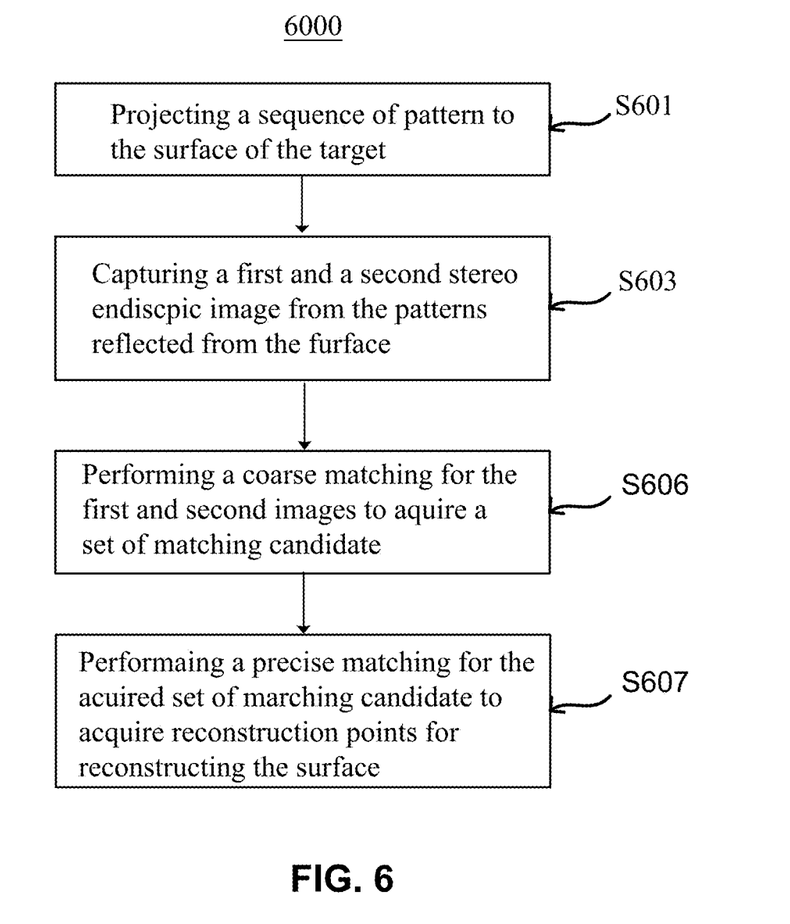
FIG. 6 illustrates a schematic view of a method for 3D surface reconstruction according to an embodiment of the present disclosure.

FIG. 6 illustrates the method 6000 for reconstructing the surface of the 3D target. At step 601, a sequence of patterns is projected to the surface of the target. At step 603, a first stereo endoscopic image and a second stereo endoscopic image are captured from the patterns reflected from the surface. At step 605, a coarse matching is performed for the captured first and second stereo endoscopic images to acquire the candidate pixels in a set of matching candidates. At step 607, a precise matching is performed for the acquired set of matching candidates to acquire reconstruction pixels for reconstructing the surface.

For the patterns to be projected, a codification strategy using two-frequency phase-shifting fringes may be utilized, wherein two frequencies $\omega^c$ and $\omega^p$ are used to generate the coarse codeword and precise codeword, respectively. It should be noted that the present disclosure is not limited to this, and multi-frequency phase-shifting fringes may also be utilized.

For the two-frequency phase-shifting fringes, the projected patterns are described by:

$$F_m^c(x,y) = A_0 + B_0 \cos(2\pi\omega^c x + \delta_m^c), (m=1,2) \quad (3)$$

$$F_n^p(x,y) = A_0 + B_0 \cos(2\pi\omega^p x + \delta_n^p), (n=1,2,3) \quad (4)$$

where $F^c$ and $F^p$ are the fringes for the coarse codeword and the precise codeword, respectively. $\delta_m^c = m \cdot \pi/2$ and $\delta_n^p = n \cdot 2\pi/3$ are the phase shifts of the two fringe sequences, respectively. (x,y) represents the coordinate of a point on the projected image. $A_0$ and $B_0$ are constant numbers.

After projected on the object, the patterns are distorted, and the corresponding captured images can be described by:

$$I_m^c(u,v)_{|k} = A(u,v)_{|k} + B^c(u,v)_{|k} \cos[\phi^c(u,v)_{|k} + \delta_m^c], (m=1,2) \quad (5)$$

$$I_n^p(u,v)_{|k} = A(u,v)_{|k} + B^p(u,v)_{|k} \cos[\phi^p(u,v)_{|k} + \delta_n^p], (n=1,2,3) \quad (6)$$

where $I_m^c$ (m=1, 2) are images for coarse codification and $I_n^p$ (n=1, 2, 3) are for precise codification, as shown in FIGS. 9A-9E, respectively. A is the texture map, which is considered to remain unchanged during the acquisition of five images. $B^c$ and $B^p$ are the intensity modulation. (u, v) is the coordinate of an arbitrary pixel on the captured image. $\phi^c$ and $\phi^p$ are phase maps, which serve as the desired coarse codeword and precise codeword, respectively. $\phi^c$ and $\phi^p$ can be derived from Eq. (7) and Eq. (8), respectively:

$$\phi^c(u,v)_{|k} = \tan^{-1} \frac{I_1^c(u,v)_{|k} - A(u,v)_{|k}}{I_2^c(u,v)_{|k} - A(u,v)_{|k}} \quad (7)$$

$$\phi^p(u,v)_{|k} = -\tan^{-1} \frac{\sum_{n=1}^{3} I_n^p(u,v)_{|k} \sin\delta_n^p}{\sum_{n=1}^{3} I_n^p(u,v)_{|k} \cos\delta_n^p} \quad (8)$$

where $A(u, v)_{|k}$ is given by:

$$A(u,v)_{|k} = \frac{I_1^p(u,v)_{|k} + I_2^p(u,v)_{|k} + I_3^p(u,v)_{|k}}{3} \quad (9)$$

In an embodiment, from the captured first and second images, the respective codeword maps may be extracted by using phases of points in the images, wherein each point in an image has a unique codeword in the codeword map. The coarse matching may be performed based on the extracted codeword maps to acquire candidate pixels in a set of matching candidates. The precise matching may be performed for the acquired candidate pixels.

In an embodiment, the projected patterns may include a coarse pattern and a precise pattern different from the coarse pattern. A first coarse image and a second coarse image may be captured from the coarse pattern reflected from the surface and a first precise image and a second precise image may be captured from the precise pattern reflected from the surface.

To perform the coarse matching, a first coarse codeword map may be extracted from the first coarse image and a second coarse codeword map from the second coarse image, and a group of points in the second coarse image corresponding to each point in the first coarse image may be determined, according to the extracted first and second coarse codeword maps so that the candidate pixels are acquired.

To perform the precise matching, a first precise codeword map is extracted from the first precise image and a second precise codeword map from the second precise image. Among the candidate pixels in the set of matching candidates, the reconstruction pixels for surface reconstruction may be determined according to the extracted first and second codeword maps.

In an embodiment, multiple coarse images (image sequence) may be captured. For example, 5 patterns (2 coarse patterns and 3 precise patterns) may be projected, and then 5 corresponding images (2 coarse images and 3 precise images) are captured by each camera. Then, one coarse codeword map may be extracted from the 2 coarse images, and one precise codeword map may be extracted from the 3 precise images.

As above, a two-step matching, i.e., a coarse matching and a precise matching are utilized in the present disclosure. The two-step matching will be described in details with reference to FIGS. 7-9.

Figure 7:
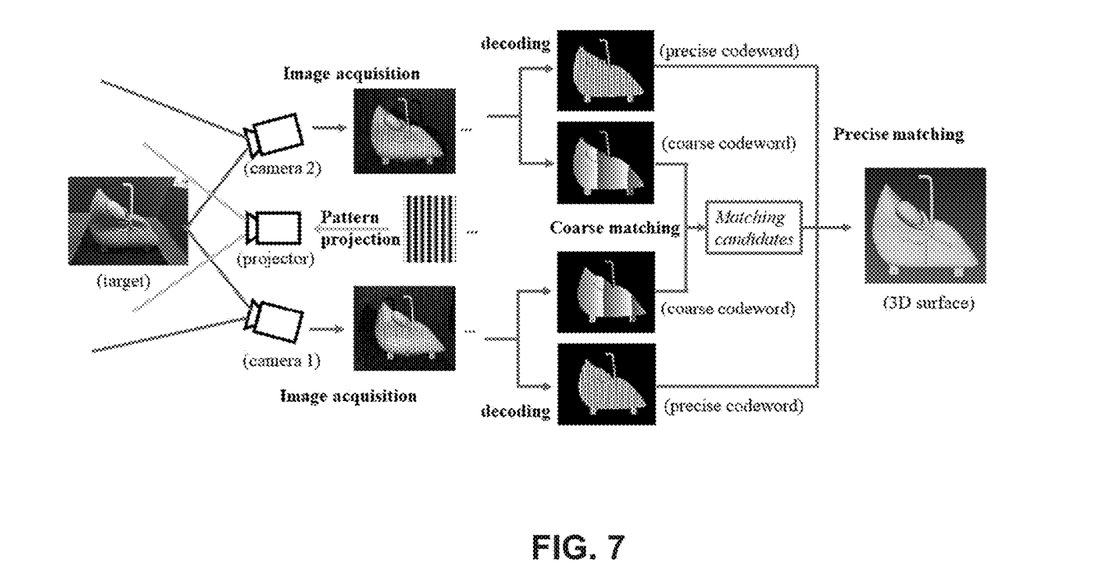
FIG. 7 illustrates a schematic view of steps of coarse and precise matching according to the present disclosure.

FIG. 7 illustrates a schematic view of steps of coarse and precise matching according to the present disclosure. FIGS. 8A-8D illustrate an exemplary procedure of the coarse and precise matching according to an embodiment of the present disclosure. FIGS. 9A-9I illustrate exemplary captured images and steps of extracting codeword maps according to an embodiment of the present disclosure. To be specific, FIG. 9A-9E illustrate the acquired images. FIG. 9F illustrates the coarse codeword map extracted from images shown in FIGS. 9A-9B. FIG. 9G illustrates the precise codeword map obtained from images shown in FIGS. 9C-9E. FIG. 9H illustrates the phases of a row of the codeword map in FIG. 9F. FIG. 9I illustrates the phases of a row of the codeword map in FIG. 9G.

A sequence of patterns is successively projected onto the target by the projecting channel. The distorted pattern images are captured by the two image capturing channels from different perspectives. The images are rectified so that each pair of corresponding pixels from two image capturing channels locates in the same epipolar line.

Coarse Codeword and Coarse Matching

From the captured images, a coarse codeword denoted as $\phi^c$ is obtained. For the coordinate (u, v) of an arbitrary pixel on the captured image, the coarse codeword $\phi^c(u, v)$ is designed to encode the whole image uniquely with low encoding accuracy. For a pixel whose coordinate on the image $(u_{|k}, v_{|k})$, its coarse codeword is represented by $\phi_{|k}^c(u_{|k}, v_{|k})$. The subscript $k \in \{l, r\}$ indicates that the images are from a left camera and a right camera (cameras 1 and 2 as shown in FIG. 7), respectively. For the sake of convenience, the coordinate ($u_{|k}$, $v_{|k}$) is also used to represent the pixel herein.

Correspondence between a left coarse codeword map $\phi_{|l}^c$ and a right coarse codeword map $\phi_{|r}^c$ should be built. For each pixel ($u_{|l}$, $v_{|l}$) on the left codeword map $\phi_{|l}^c$, a pixel ($u_{|r}$, $v_{|r}$) from the right camera is regarded as one of the correspondence candidates of the pixel ($u_{|l}$, $v_{|l}$) if it satisfies $|\phi_{|l}^c(u_{|l}, v_{|l}) - \phi_{|r}^c(u_{|l}, v_{|l})| < \xi$, where $\xi$ is a user defined small constant. A set of all the correspondence candidates is denoted as ($U_{|r}$, $v_{|r}$), as shown in FIG. 8B. Since the coarse codeword encodes the whole image uniquely, at most one group of connected pixels can be found as the corresponding candidates for each pixel from left camera. This step is called coarse matching, as shown FIGS. 8A and 8B.

Figure 8A:
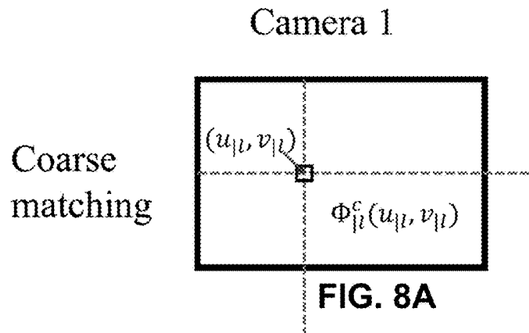
FIGS. 8A-8D illustrate an exemplary procedure of the coarse and precise matching according to an embodiment of the present disclosure.
Figure 8B:
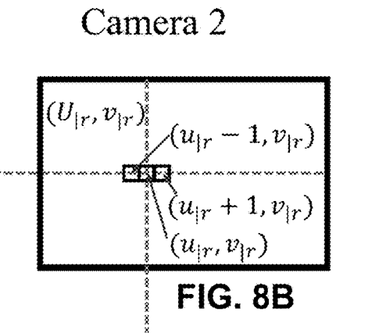
Figure 9A:
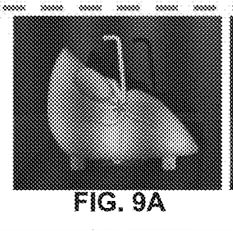
FIGS. 9A-9I illustrate exemplary captured images and steps of extracting codeword maps according to an embodiment of the present disclosure.
Figure 9B:
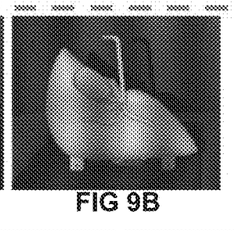
Figure 9C:
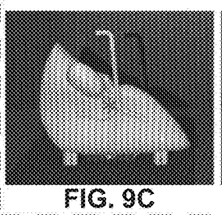
Figure 9D:
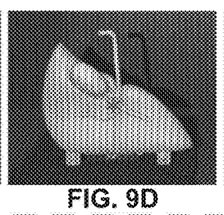
Figure 9E:
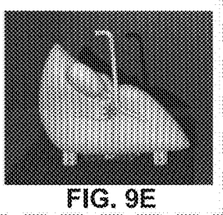
Figure 9F:
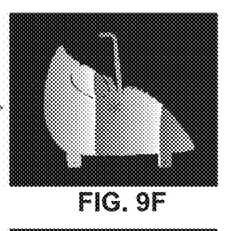
Figure 9G:
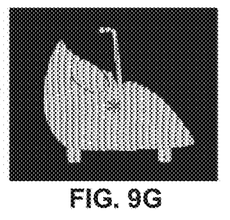
Figure 9H:
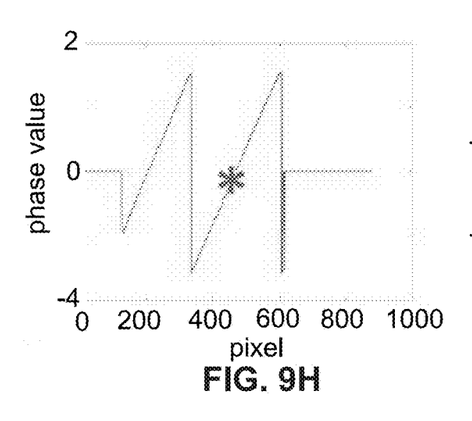
Figure 9I:
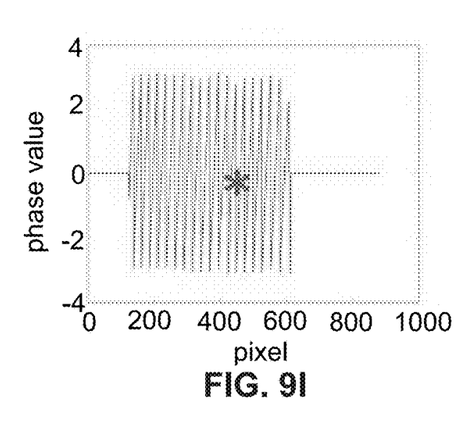

With reference to FIGS. 8A-8B, a pixel ($u_{|l}$, $v_{|l}$) on the left coarse codeword map (as shown in FIG. 8A) has a coarse codeword $\phi_{|l}^c(u_{|l}, v_{|l})$, and the correspondence candidates are denoted as ($U_{|l}$, $v_{|l}$) on the right coarse codeword map as shown in FIG. 8B.

Figure 10:
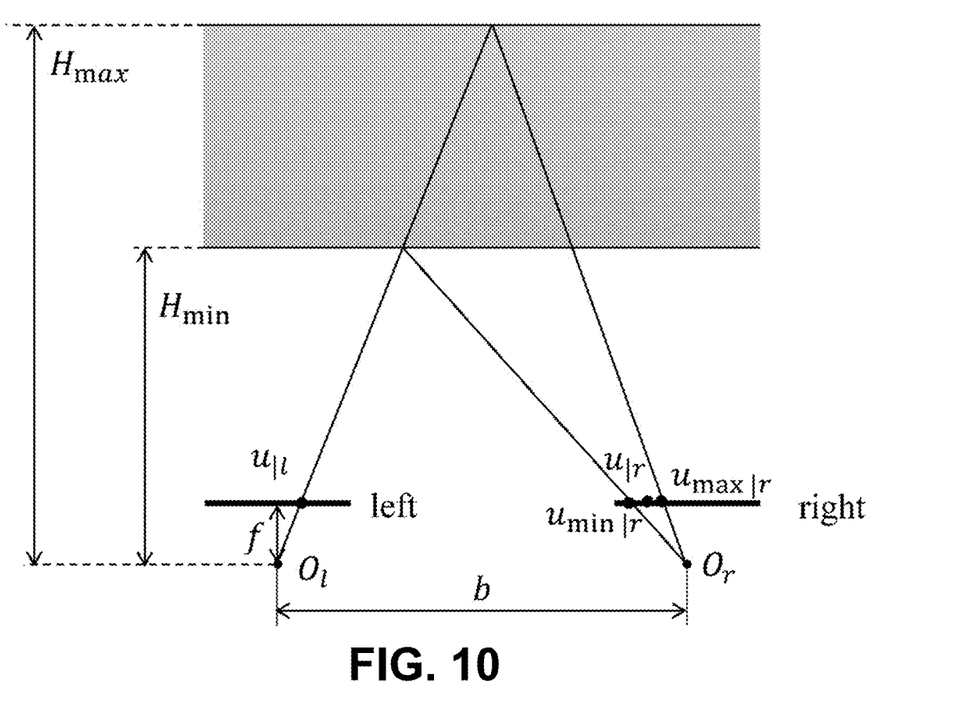
FIG. 10 illustrates a view of geometry constraint of two image capturing devices according to an embodiment of the present disclosure.

For the coarse codeword, since an arctangent function is used in Eq. (8), the obtained phases have a problem of $2\pi$ discontinuity, as shown in FIG. 9H. The $2\pi$ discontinuity will lead to ambiguity in the correspondence establishment. To prevent the ambiguity, a geometry constraint is introduced as illustrated in FIG. 10. Suppose the measured range in the depth direction [Hmin, Hmax] is known, then for any pixel on the left image whose u coordinate is u|l, the u coordinate of its corresponding pixel on the right image will always locate in a closed interval [umin|r, umax|r]. The relationship is given by:

$$u_{min|r} = u_{|r} - \frac{bf}{H_{min}} \tag{10}$$

$$u_{max|r} = u_{|r} - \frac{bf}{H_{max}} \tag{11}$$

where b and f are the baseline between the two cameras and the focal length, respectively. Let the period of the coarse codeword Tc equal to the range $u_{max|r} - u_{min|r} = bf/H_{min} - bf/H_{max}$ which is a fixed value, then the ambiguity can be removed. FIG. 10 illustrates a view of geometry constraint of two image capturing devices according to an embodiment of the present disclosure. As shown in FIG. 10, $O_l$ and $O_r$ represent projection centers of the left and right cameras, respectively. The depth range is [$H_{min}$, $H_{max}$]. If the projection of a point on the left plane is $u^P$, its projection on the right image $u^P$ is limited to [$u_{min|r}$, $u_{max|r}$].

Among the correspondence candidates, the precise matching is performed, which will be described in details as follows.

Precise Codeword and Precise Matching

For a pixel whose coordinate on the image ($u_{|k}$, $v_{|k}$), its precise codeword is represented by $\phi_{|k}^P(u_{|k}, v_{|k})$. The subscript $k \in \{l, r\}$ indicates that the images are from cameras 1 and 2 shown in FIG. 7 (may be referred as to a left camera and a right camera hereinafter), respectively.

The precise codeword is designed to encode the corresponding candidates decided by the coarse codeword.

Among the correspondence candidates ($U_{|r}$, $v_{|r}$), pixel with the minimum value of $|\phi_{|l}^P(u_{|l}, v_{|l}) - \phi_{|r}^P(u_{|r}, v_{|r})|$ is regarded as the best corresponding pixel. This step is called precise matching.

Figure 8C:
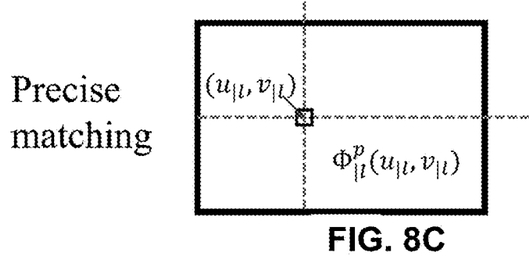
Figure 8D:
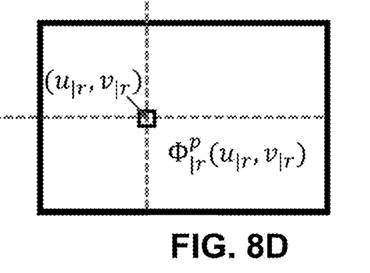

As shown in FIGS. 8C and 8D, pixel ($u_{|l}$, $v_{|l}$) on the left precise codeword map (as shown in FIG. 8C) has a precise codeword $\phi_{|l}^P(u_{|l}, v_{|l})$, and the best corresponding point ($u_{|r}$, $v_{|r}$) on the right precise codeword (as shown in FIG. 8D), whose precise codeword $\phi_{|r}^P(u_{|r}, v_{|r})$ is the closest to $\phi_{|l}^P(u_{|l}, v_{|l})$ among the candidates.

To assign each candidate with unique phase value, the period of the precise phase $T^p$ should be larger than the maximum range of the u coordinates of the candidates, which is $\xi T^c/\pi$. Therefore, it is reasonable to choose the period of precise codeword as ceil($\xi T^c/\pi$).

The advantages of the proposed two-step matching are from the following aspects:

1. Fast speed and high accuracy: Instead of searching for precise correspondence across the whole image, the proposed method builds rough correspondence quickly, and finds precise correlation in local pixels, which reduces the matching time and achieves high accuracy reconstruction.

2. Low algorithm complexity: The matching criterion is realized by simple addition and subtraction, which reduces the algorithm complexity.

With the proposed method, only five patterns are required, which is much less than the common codification methods. At the same time, the high accuracy is inherited from the high-frequency phase shifting fringes. Moreover, since the precise codeword encodes local pixels, the complex phase unwrapping is avoided.

Correspondence Refinement

In the above, the correspondence points are assumed always to be located exactly on the pixels of the right image. However, since a pixel is a discrete sample of the continuous original image, most of the correspondence points locate between two pixels. Therefore, we propose a refinement algorithm to estimate the true position of the correspondence point.

With the two-step matching method described as above, the best correspondence ($u_{|r}$, $v_{|r}$) of a pixel ($u_{|l}$, $v_{|l}$) is obtained. Theoretically the true position of the correspondence point is considered to be located at the neighborhood of the pixel ($u_{|r}$, $v_{|r}$), whose phase values can be estimated by the Taylor series shown in Eq. (12). The higher order items are ignored.

$$\phi_{|r}^P(u) = \phi_{|r}^P(u_{|r}) + \frac{\partial \phi_{|r}^P}{\partial u}(u - u_{|r}) + \frac{1}{2}\frac{\partial^2 \phi_{|r}^P}{\partial u^2}(u - u_{|r})^2 \tag{12}$$

where $$\frac{\partial \phi_{|r}^P}{\partial u} = \phi_{|r}^P(u_{|r}, v_{|r}) - \phi_{|r}^P(u_{|r} - 1, v_{|r}) \tag{13}$$

$$\frac{\partial^2 \phi_{|r}^P}{\partial u^2} = \phi_{|r}^P(u_{|r} - 1, v_{|r}) - 2\phi_{|r}^P(u_{|r}, v_{|r}) + \phi_{|r}^P(u_{|r} + 1, v_{|r}) \tag{14}$$

Let Eq. (12) equal to the $\phi_{|l}^P(u_{|l}, v_{|l})$, the estimated true correspondence can be obtained by solving for the quadratic equation. Although there are two solutions for the quadratic equation, only one locates within the neighbors of ($u_{|r}$, $v_{|r}$). Therefore, unique correspondence can be found in the refinement.

Figure 11A:
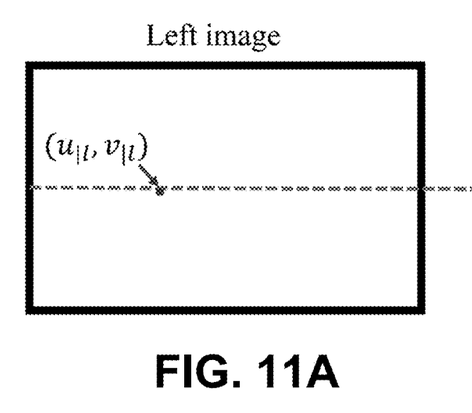
FIGS. 11A and 11B illustrate true positions of corresponding points in the captured images according to an embodiment of the present disclosure.
Figure 11B:
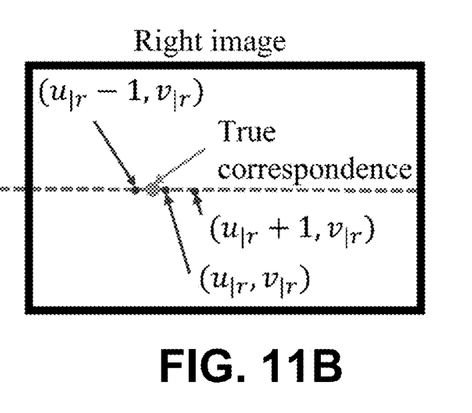

FIGS. 11A and 11B illustrate true positions of corresponding points in the captured images according to an embodiment of the present disclosure. For the pixel ($u_{|l}$, $v_{|l}$) on the left image shown in FIG. 11A, the obtained corresponding pixel ($u_{l_r}$, $v_{l_r}$) on the right image is shown in FIG. 11B, and the true corresponding point can be obtained by correspondence refinement.

Hereinafter, comparative experiments are illustrated to validate the accuracy and efficiency of the system and method proposed in the present disclosure.

Figure 12A:
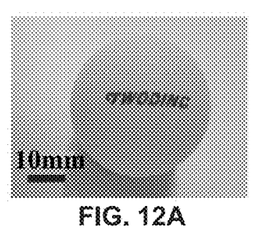
FIGS. 12A-12H illustrate comparative experimental results of 3D surface reconstruction by using the method of the present disclosure and the current RPC method.
Figure 12B:
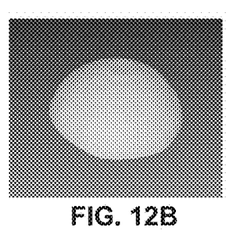
Figure 12C:
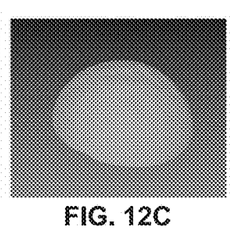
Figure 12D:
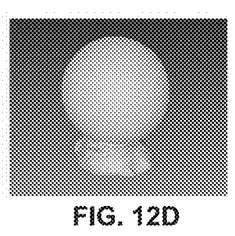
Figure 12E:
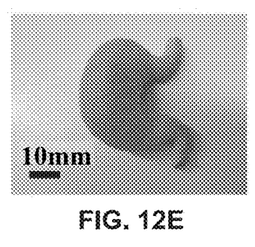

FIGS. 12A-12H illustrate comparative experimental results of 3D surface reconstruction by using the method of the present disclosure and the current pseudo-random patterns codification (RPC) method. FIG. 12A is a photography of a ping-pong ball. FIG. 12B illustrates the reconstructed surface of the ping-pong ball using the proposed two-step matching method. FIG. 12C illustrates the reconstructed surface of the ping-pong ball using the RPC method. FIG. 12D illustrates the ground-truth of the ping-pong ball. FIG. 12E is a photography of a stomach model.

Figure 12F:
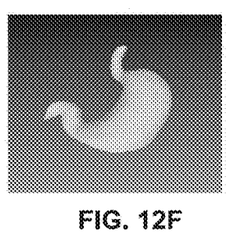
Figure 12G:
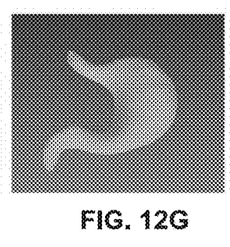
Figure 12H:
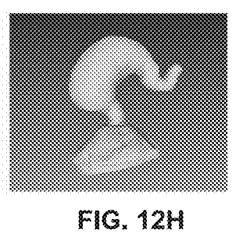

FIG. 12F illustrates the reconstructed surface of the stomach model using the proposed two-step matching method. FIG. 12G illustrates the reconstructed surface of the stomach model using the RPC method. FIG. 12H illustrates the ground-truth of the stomach model.

For the ping-pong ball shown in FIG. 12A and the stomach model shown in FIG. 12E, the resulting reconstructed surfaces of the two objects using the proposed method are illustrated in FIGS. 12B and 12F, respectively. The corresponding surfaces using RPC method are plotted in FIGS. 12C and 12G, respectively. FIGS. 12D and 12H demonstrate the ground truth of both models, respectively. For the stomach model, the average error of the reconstructed surface using the proposed method is 0.166 mm, while that of the RPC method is 0.190 mm. The average errors of the reconstructed ping-pong ball surface using the proposed method and RPC method are 0.136 mm and 0.157 mm, respectively. It can be obtained that our proposed method has comparable accuracy with the mature time-multiplexing technique. The time cost of 3D surface measurement using the proposed method is 87 ms and 88 ms for stomach model and ping-pong ball, respectively, which are three times shorter than those using RPC method (342 ms and 354 ms, respectively). The efficiency of 3D reconstruction is largely improved with the proposed the proposed method To verify the performance of the proposed method in biological material surface reconstruction, an Ex-vivo experiment is conducted.

Figure 13A:
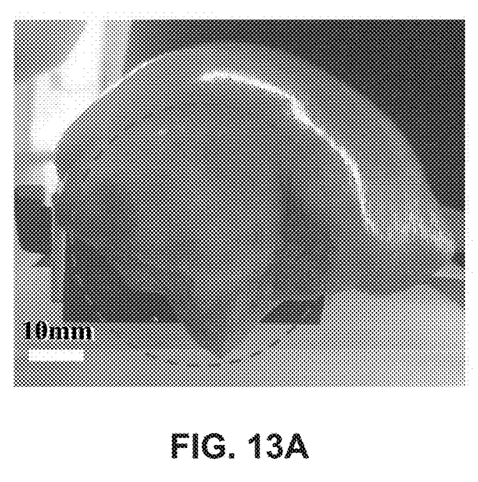
FIGS. 13A-13B illustrate an exemplary Ex-vivo experiment results using the system and method of 3D laparoscopic surface reconstruction according to an embodiment of the present disclosure.
Figure 13B:
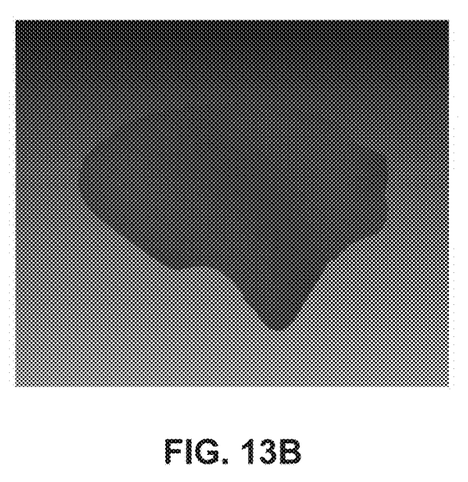

FIGS. 13A-13B illustrates an exemplary Ex-vivo experiment results using the system and method of 3D laparoscopic surface reconstruction according to an embodiment of the present disclosure, wherein a porcine liver is measured in the experiment. FIG. 13A is a photography of a porcine liver, the measured area is circled by the dotted line. FIG. 13B illustrates the reconstructed surface of the porcine liver.

The FOV for 3D reconstruction is marked by the circle, whose diameter is around 40 mm. The corresponding reconstructed surfaces are shown in FIG. 13B. It is observed that the reconstruction result agrees with the organ by comparing the distinctive morphology including the shape of the model, the surface continuity, the relative height variation and the steep steps on the border, etc. Besides, it verifies that the algorithm has the robustness to the homogeneous texture of the organs.

Figure 14:
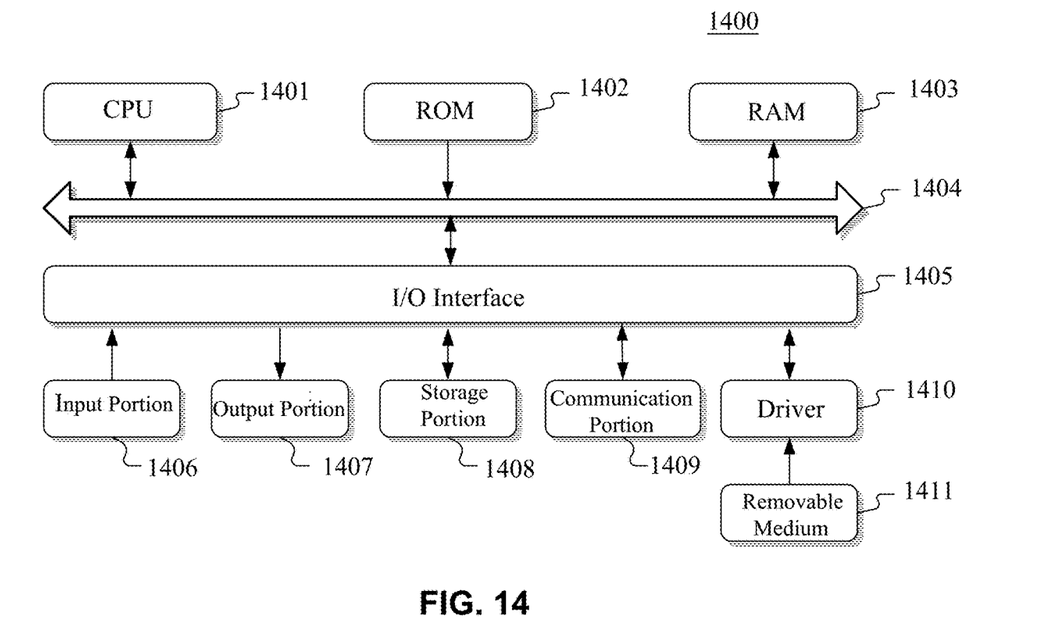
FIG. 14 illustrates a schematic structural diagram of a computer system adapted to implement the embodiments of the present disclosure.

FIG. 14 illustrates a schematic diagram of a computer system adapted to implement embodiments of the present disclosure.

With reference to FIG. 14, a schematic diagram of a computer system 1400 adapted to implement the embodiments of the present disclosure is illustrated. The computer system shown in FIG. 14 is merely an example and should not impose any restriction on the functions and the scope of use of the embodiments of the present disclosure. The computer system 1400 may be used, for example, to implement a portion of one or more components used for a pattern generating device, a map extracting device or a reconstructing device. Computer system is known to those skilled in the art and thus is described briefly herein.

As shown in FIG. 14, the computer system 1400 includes a central processing unit (CPU) 1401, which may execute various appropriate actions and processes in accordance with a program stored in a read-only memory (ROM) 1402 or a program loaded into a random access memory (RAM) 1403 from a storage portion 1408. The RAM 1403 also stores various programs and data required by operations of the system 1400. The CPU 1401, the ROM 1402 and the RAM 1403 are connected to each other through a bus 1404. An input/output (I/O) interface 1405 is also connected to the bus 1404.

The following components are connected to the I/O interface 1405: an input portion 1406 including a keyboard, a mouse, etc.; an output portion 1407 including such as a cathode ray tube (CRT), a liquid crystal display (LCD) and a loudspeaker, etc.; a storage portion 1408 including a hard disk and the like; and a communication portion 1409 comprising a network interface card, such as a LAN card and a modem. The communication portion 1409 performs communication processes via a network, such as the Internet. A drive 1410 is also connected to the I/O interface 1405 as required. A removable medium 1411, such as a magnetic disk, an optical disk, a magneto-optical disk, a semiconductor memory, is installed on the drive 1410 as needed, to facilitate the retrieval of a computer program from the removable medium 1411, and the installation thereof on the storage portion 1408 as needed.

In particular, according to the embodiments of the present disclosure, the process described above with reference to the flowchart may be implemented in a computer software program. For example, the embodiments of the present disclosure include a computer program product, which comprises a computer program that is embedded in a computer readable medium. The computer program comprises program codes for executing the method as illustrated in the flowchart. In such embodiments, the computer program may be downloaded and installed from a network via the communication portion 1409, and/or be installed from the removable media 1411. The computer program, when executed by the central processing unit (CPU) 1401, implements the above mentioned functionalities as defined by the method of the present disclosure.

It should be noted that the computer readable medium in the present disclosure may be computer readable storage medium. An example of the computer readable storage medium may include, but not limited to semiconductor systems, apparatus, elements, or a combination any of the above. A more specific example of the computer readable storage medium may include but is not limited to: electrical connection with one or more wire, a portable computer disk, a hard disk, a random access memory (RAM), a read only memory (ROM), an erasable programmable read only memory (EPROM or flash memory), a fibre, a portable compact disk read only memory (CD-ROM), an optical memory, a magnet memory or any suitable combination of the above. In the present disclosure, the computer readable storage medium may be any physical medium containing or storing programs which can be used by a command execution system, apparatus or element or incorporated thereto. The computer readable medium may be any computer readable medium except for the computer readable storage medium. The computer readable medium is capable of transmitting, propagating or transferring programs for use by, or used in combination with, a command execution system, apparatus or element. The program codes contained on the computer readable medium may be transmitted with any suitable medium including but not limited to: wireless, wired, optical cable, RF medium etc., or any suitable combination of the above.

The flowcharts and block diagrams in the accompanying drawings illustrate system architectures, functions and operations that may be implemented according to the system, the method and the computer program product of the various embodiments of the present disclosure. In this regard, each block in the flowcharts and block diagrams may represent a module, a program segment, or a code portion. The module, the program segment, or the code portion comprises one or more executable instructions for implementing the specified logical function. It should be noted that, in some alternative implementations, the functions denoted by the blocks may also occur in a sequence different from the sequences shown in the figures. For example, in practice, two blocks in succession may be executed, depending on the involved functionalities, substantially in parallel, or in a reverse sequence. It should also be noted that, each block in the block diagrams and/or the flowcharts and a combination of the blocks in the block diagrams and/or the flowcharts may be implemented by a dedicated hardware-based system executing specific functions or operations, or by a combination of a dedicated hardware and computer instructions.

The devices involved in the embodiments of the present disclosure may be implemented by way of software or hardware. The described devices may also be provided in a processor, for example, described as a pattern generating device, a map extracting device or a reconstructing device. Here, the names of these devices are not considered as limitations to the devices in certain circumstances.

In another aspect, the present disclosure further provides a computer readable medium. The computer readable medium may be included in the computer system described in the above embodiments, or a stand-alone computer readable medium which has not been assembled into the computer system. The computer readable medium carries one or more programs.

The foregoing is only a description of the preferred embodiments of the present disclosure and the applied technical principles. It should be appreciated by those skilled in the art that the inventive scope of the present disclosure is not limited to the technical solutions formed by the particular combinations of the above technical features. The inventive scope should also cover other technical solutions formed by any combinations of the above technical features or equivalent features thereof without departing from the concept of the invention, such as, technical solutions formed by replacing the features as disclosed in the present disclosure with (but not limited to), technical features with similar functions.

The above are merely optional embodiments of the present disclosure. A person skilled in the art may make modifications and improvements to those embodiments without departing from the principle of the present disclosure, and these modifications and improvements shall also fall within the scope of the present disclosure.

What is claimed is:

1. A method for reconstructing a surface of a three-dimensional (3D) target, comprising:
    projecting a sequence of patterns to the surface of the target;
    capturing a first stereo endoscopic image and a second stereo endoscopic image from the patterns reflected from the surface;
    extracting respective codeword maps from the captured first and second stereo endoscopic images, wherein each point in the captured images has a unique codeword in the codeword map;
    performing a coarse matching for the captured first and second stereo endoscopic images to acquire a set of matching candidates; and
    performing a precise matching for the acquired set of matching candidates to acquire reconstruction pixels for reconstructing the surface, wherein the coarse matching is performed based on the extracted codeword maps to acquire candidate pixels in the set of matching candidate; and the precise matching is performed among the acquired candidate pixels.

2. The method according to claim 1, wherein the extracting further comprises:
    extracting respective codeword maps from the captured first and second stereo endoscopic images by using phases of points in the images.

3. The method according to claim 1, wherein the projected patterns include a coarse pattern, and the capturing includes:
    capturing a first coarse image and a second coarse image from the coarse pattern reflected from the surface.

4. The method according to claim 3, wherein the extracting respective codeword maps from the captured first and second stereo endoscopic images comprises:
    extracting a first coarse codeword map from the first coarse image and a second coarse codeword map from the second coarse image; and
    the performing a coarse matching comprises:
        determining, according to the extracted first and second coarse codeword maps, a group of points in the second coarse image corresponding to each point in the first coarse image, to acquire candidate pixels in the set of matching candidate.

5. The method according to claim 4, wherein the projected patterns further include a precise pattern different from the coarse pattern, and the capturing further comprises:
    capturing a first precise image and a second precise image from the precise pattern reflected from the surface.

6. The method according to claim 5, wherein the extracting respective codeword maps from the captured first and second stereo endoscopic images comprises:
    extracting a first precise codeword map from the first precise image and a second precise codeword map from the second precise image; and
    the performing a precise matching comprises:
        determining, among the acquired candidate pixels in the set of matching candidate in the coarse matching, the reconstruction pixels for surface reconstruction according to the extracted first and second codeword maps.

7. The method according to claim 1, wherein the generated patterns are multi-frequency phase shifting fringes, and wherein the coarse pattern is a phase shifting fringe with a frequency lower than that of the precise pattern.

8. The method according to claim 1, wherein the codeword maps are wrapped phase maps derived from the captured stereo images.

9. A system for reconstructing a surface of a three-dimensional (3D) target, comprising:
- a pattern projecting device for projecting a sequence of patterns to the surface of the target;
- an image capturing device for capturing a first stereo endoscopic image and a second stereo endoscopic image from the patterns reflected from the surface;
- a reconstructing device for performing a coarse matching for the captured first and second stereo endoscopic images to acquire a set of matching candidates, and performing a precise matching for the acquired set of matching candidate to acquire pixels for reconstructing the surface, and
- a map extracting device for extracting respective codeword maps from the captured first and second stereo endoscopic images, wherein each point in the captured images has a unique codeword in the codeword map,
- wherein the coarse matching is performed based on the extracted codeword maps to acquire candidate pixels in the set of matching candidate; and the precise matching is performed among the acquired candidate pixels.

10. The system according to claim 9, wherein the map extracting device is further configured to extract respective codeword maps from the captured first and second stereo endoscopic images by using phases of points in the images.

11. The system according to claim 9, further comprising:
- a pattern generating device for generating a coarse pattern, and the image capturing device is configured to capture a first coarse image and a second coarse image from the coarse pattern reflected from the surface.

12. The system according to claim 11, wherein the map extracting device is further configured for:
- extracting a first coarse codeword map from the first coarse image and a second coarse codeword map from the second coarse image; and
- the reconstructing device is configured to perform the coarse matching by:
  - determining a group of points in the second coarse image corresponding to each point in the first coarse image, according to the extracted first and second coarse codeword maps to acquire candidate pixels in the set of matching candidate.

13. The system according to claim 12, wherein the pattern generating device is further configured to generate a precise pattern different from the coarse pattern, and the image capturing device is configured to capture a first precise image and a second precise image from the precise pattern reflected from the surface.

14. The system according to claim 13, wherein the map extracting device is further configured for:
- extracting a first precise codeword map from the first precise image and a second precise codeword map from the second precise image; and
- the reconstructing device is configured to perform the precise matching by:
  - determining, among the acquired candidate pixels in the set of matching candidate, the reconstruction pixels for surface reconstruction according to the extracted first and second codeword maps.

15. The system according to claim 9, wherein the generated patterns are multi-frequency phase shifting fringes, and wherein the coarse pattern is a phase shifting fringes with a frequency lower than that of the precise pattern.

16. The system according to claim 9, wherein the pattern projecting device is a digital light processing (DLP) projector and the image capturing device is a high-speed camera.

17. A system for reconstructing a surface of a three-dimensional (3D) target, comprising:
- a pattern projecting device for projecting a sequence of patterns to the surface of the target;
- an image capturing device for capturing a first stereo endoscopic image and a second stereo endoscopic image from the patterns reflected from the surface;
- at least one processor; and
- a memory storing instructions, the instructions when executed by the at least one processor, cause the at least one processor to perform operations, the operations comprising:
- generating the patterns to be projected including a coarse pattern and a precise pattern;
- extracting respective codeword maps from the captured first and second stereo endoscopic images by using phases of points in the images, wherein each point in an image has a unique codeword in the codeword map; and
- performing a coarse matching for the captured first and second stereo endoscopic images to acquire a set of matching candidates, and performing a precise matching for the acquired set of matching candidate to acquire reconstruction pixels for reconstructing the surface.

18. The system according to claim 17, wherein the pattern projecting device is a digital light processing (DLP) projector and the image capturing device includes two high-speed cameras for capturing the first and second stereo endoscopic image, respectively.

\* \* \* \* \*